United States Patent
Bojrab

(10) Patent No.: US 7,901,925 B2
(45) Date of Patent: Mar. 8, 2011

(54) LACTOBACILLUS DELBRUECKII SSP. BULGARICUS STRAIN AND COMPOSITIONS

(76) Inventor: Gregory G. Bojrab, Indianapolis, IN (US)

( * ) Notice: Subject to any disclaimer, the term of this patent is extended or adjusted under 35 U.S.C. 154(b) by 519 days.

(21) Appl. No.: 11/473,654

(22) Filed: Jun. 23, 2006

(65) Prior Publication Data

US 2007/0298019 A1    Dec. 27, 2007

(51) Int. Cl.
*C12N 1/20* (2006.01)
*A01N 63/00* (2006.01)

(52) U.S. Cl. .................................. 435/252.9; 424/93.45

(58) Field of Classification Search ........................ None
See application file for complete search history.

(56) References Cited

U.S. PATENT DOCUMENTS 6,641,808 B1 * 11/2003 Bojrab .......................... 424/93.3

OTHER PUBLICATIONS http://www.lacpro.com/about_probiomax.html, accessed Aug. 27, 2008 (About Pro.Bio.MAX™ Smoothies:).*
Shihata et al., International Dairy Journal 10 (2000) 401-408.*
Vinderola et al., J. Dairy Sci. 85:721-729.*

* cited by examiner

Primary Examiner — Irene Marx
(74) Attorney, Agent, or Firm — Ice Miller LLP

(57) ABSTRACT

A novel strain of *Lactobacillus delbrueckii*, ssp. *bulgaricus*, including probiotic compositions comprising the bacteria, and methods for using the bacteria and/or the compositions for treatments of diseased states and boosting immune response.

10 Claims, 2 Drawing Sheets

LACTOBACILLUS DELBRUECKII SSP. BULGARICUS STRAIN AND COMPOSITIONS

FIELD OF THE INVENTION

The present application relates generally to a novel organism strain, compositions comprising the novel organism, and methods of using the organism as a probiotic. Probiotics are defined by the World Health Organization as "live microorganisms, which when administered in adequate amounts confer a health benefit on the host."

BACKGROUND

The human digestive tract is an ecosystem unto itself, containing a complex diversity of beneficial and harmful bacteria, with over 400 different bacteria species being found in the intestine alone. This diverse intestinal microflora plays a substantial role in regulating intestinal barrier defense mechanism, and effectively comprises approximately 80% of our immune system. Ongoing research continues to support the theory that appropriate microbial balance in the intestine greatly enhances the general health and immune system of a person or animal when compared to another individual lacking such a balance.

As noted above, a healthy population of beneficial, mutualistic, and/or commensal microorganisms in the digestive tract play a substantial role in maintaining the health and welfare of the host organism. Such microorganisms create benefits to their hosts in many ways: through competition with pathogenic microorganisms, aiding in the digestion and absorption of food, helping with vitamin synthesis, and regulating immune responses. Therefore, healthy individuals often display a robust collection of beneficial microorganisms in their digestive systems, which aid them in maintaining a disease free state, and further contribute to the overall well-being of the individual.

However, over the ordinary course of a lifetime, disruptive events can lead to an imbalance in the ecology of the digestive tract, leading to a non-ideal balance of diversity and populations of beneficial microorganisms therein. Such disruptive events include illnesses caused by exposure to viruses or pathogenic microorganisms; exposure to certain pharmaceuticals, including antibiotics; exposure to high levels of mental, physical, or emotional stress, including surgical complications or excessive travel; and improper nutrition or malnutrition. In addition, studies have shown that as individuals age, the stability of the delicate balance of intestinal flora declines, which can lead to an unhealthy imbalance in the digestive tract that may weaken the immune system and/or give rise to the possibility of infection, autoimmune dysfunction, and several surprising downstream biological system problems.

Thus, a healthy, balanced digestive tract flora is important to ensure that an individual maintains a state of health. Further, it has been shown that the use of transitory microorganisms, or microorganisms that are not commonly found in the digestive tract, but may be introduced for short periods of time, can help restore a balance of beneficial flora in otherwise healthy individuals, can combat pathogenic microorganisms and viruses, and can cause surprising positive effects in a host. For example, U.S. Pat. No. 6,696,057, incorporated by reference herein, discusses the successful use of a probiotic composition comprising two microorganisms that has been shown to reduce hyperlipidemia (high cholesterol); combat autoimmune diseases; alleviate Irritable Bowel Syndrome, Inflammatory Bowel Disease, and diarrhea; reduce the symptoms of Crohn's disease; and treat ulcerative colitis. When compared to traditional treatments, the use of such probiotic compositions were far less expensive, showed fewer side effects in the individuals tested, and showed the positive side effect of reducing inflammatory response in the digestive tract, which may aid in a reduction of the risk of colorectal cancer or other diseases.

While the composition disclosed in U.S. Pat. No. 6,696,057 and comprising *Streptococcus thermophilus* and *Lactobacillus delbrueckii*, ssp. *bulgaricus* (also referred to as "*Lactobacillus bulgaricus*") has been shown to be effective, finding and maintaining ideal culture conditions to maximize production of these two different species in a consumable media can be difficult. In addition, it would be greatly appreciated if a single species or strain of a species could be identified that displays the same or similar host biological response and effectiveness in treating the aforementioned illnesses, as well as boosting immune system response. Further, an organism or strain that would produce the target pH and target number of culture forming units in less time than *Streptococcus thermophilus* and/or *Lactobacillus bulgaricus*, would be greatly appreciated in the art.

SUMMARY

The present application relates to an isolated strain of *Lactobacillus*, compositions including the strain or culture, and methods for its use. Specifically, according to one embodiment, the present application relates to an isolated culture of a bacterial strain *Lactobacillus delbrueckii*, ssp. *bulgaricus* having accession number NRRL B-30892. According to one aspect, the isolated culture described may further be placed in freeze-dried form. It will be appreciated that in another embodiment, the isolated culture may comprise at least 3×10 e10 colony forming units. Further, the isolated culture may further comprise a culture media that can increase the CFU of the isolated culture. One embodiment utilizes a dairy product, while other embodiment use animal or plant-based milk products.

It will be appreciated that one embodiment of the present application relates to an isolated culture of a bacterial strain of the genus *Lactobacillus*, with the following characteristics as exhibited by the culture deposited in the Agricultural Research Service Patent Culture Collection and given the NRRL Accession Number B-30892: efficiency in multiplying in dairy products and an ability to continue production of colony forming units below a pH of 4.5. Furthermore another embodiment of the present application involves a probiotic composition comprising the bacteria strain described within this application, along with a delivery mechanism. It will be appreciated that in one embodiment of the present application, the delivery mechanism comprises a carbohydrate-containing medium operable to increase the culture size of an inoculation dose of the bacteria described herein. In yet another embodiment, the inoculation dose may increase in size to a therapeutic dose of the bacteria described herein in the carbohydrate-containing medium. Further, the carbohydrate-containing medium is optionally a milk-based product and the milk-based product can optionally be a vegetable milk or a milk derived or taken from an animal. Additionally, it should be noted that one embodiment utilizes at least about 1.3×10e10 CFU as a therapeutic dose of the bacteria strain described herein. Other embodiments utilize at least about 3×10e10 colony forming units as a therapeutic dose. Further, it will be appreciated that varying different volumes of the probiotic composition may include a therapeutic dose of the bacteria strain. For example, according to one embodiment, the therapeutic dose of the bacteria strain is found in about 10 ounces or less or the composition. In other embodiments, the therapeutic dose may be about 8 ounces or less of the composition, or 3 ounces or less of the composition. In addition, according to one embodiment, the probiotic composition displays the characteristic of alleviating symptoms of a diseased state. For example, the probiotic composition may provide alleviation of symptoms of Crohn's disease, ulcerative colitis, irritable bowel syndrome, inflammatory bowel disease, diarrhea, hyperlipidemia, hypovitaminosis, antibiotic-associated diarrhea, or CDAD. It will be appreciated that other delivery mechanisms may be used, such as utilizing a container operable to maintain the bacteria strain in a freeze-dried form, or in which the bacteria may be encapsulated for ingestion.

According to another embodiment, the present application relates to a method for augmenting an animal's immune system, the method comprising the steps of providing a therapeutically effective amount of a probiotic composition comprising the bacteria strain described herein and administering the therapeutically effective amount of the bacteria to the animal through ingestion. In one embodiment, a therapeutically effective amount of the probiotic composition is an amount sufficient to prevent an establishment of pathogenic organisms in the animal for a predetermined period of time. In another embodiment, the therapeutically effective amount of the bacteria comprises a range of about $1.5 \times 10e10$ to about $5 \times 10e10$ colony forming units. Further, the therapeutically effective amount of the bacteria may be further mixed within a carbohydrate enriched media. According to certain embodiments, the therapeutically effective amount of the bacteria, when mixed with the carbohydrate enriched media, comprises approximately 10 ounces or less. In certain embodiments, the effective amount of the bacteria is administered to the animal at least twice per day. Optionally, at least three hours may elapse between each administration of the therapeutically effective amount of the bacteria. In addition, according to one embodiment, the method includes the step of providing an animal showing symptoms of gastrointestinal disorders, hyperlipidemia, or autoimmune diseases. According to another embodiment, the method includes the step of providing an animal showing symptoms of a diseased state selected from the group consisting of Crohn's disease, ulcerative colitis, irritable bowel syndrome, inflammatory bowel disease, diarrhea, and CDAD.

According to another embodiment, the present application relates to a method for augmenting an animal's immune system, the method comprising the steps of providing a probiotic composition comprising at least $3 \times 10e10$ CFU of the bacteria described herein, and not more than 12 ounce of a carbohydrate-containing medium, administering the probiotic composition to an animal showing symptoms of at least one diseased state selected from the group consisting of Crohn's disease, ulcerative colitis, irritable bowel syndrome, inflammatory bowel disease, diarrhea, and CDAD, and repeating administration of the probiotic composition at least twice daily at least until subsistence of the symptoms, with repeated administration occurring at an interval not less than two hours after a previous administration of the probiotic composition. In addition, according to one embodiment, the carbohydrate-containing medium is a milk-based product operable to increase an inoculating colony of the bacteria to at least $3 \times 10e10$ CFU of the bacteria per less than about twelve ounce of the carbohydrate-containing medium. Optionally, the probiotic composition is a cultured beverage or smoothie.

Yet another embodiment involves a method of treating a diseased state in a patient using a probiotic composition, with the method comprising the following steps: providing a probiotic composition comprising a specified number of CFU of the bacteria described herein, a carbohydrate-containing medium wherein the specified CFU of the bacteria are combined and allowed to ferment until a desired number of total CFU per dose is achieved; administering the probiotic composition to a patient showing symptoms of at least one diseased state selected from the group consisting of Crohn's disease, ulcerative colitis, irritable bowel syndrome, inflammatory bowel disease, diarrhea, hyperlipidemia, hypovitaminosis, autoimmune disease, and CDAD; selecting a dosing form of the probiotic composition; determining an initial dosing number of CFU of the bacteria for a given dose; determining an initial dosing frequency; determining the efficacy of the probiotic composition in treating the patient's disease or diseased state; adjusting the dosing number, if required, to effectuate positive results in the patient; and adjusting the dosing frequency, if required, to effectuate a positive result in the patient. Optionally, the initial dosing number of colony forming units per dose may range from about $1 \times 10e10$ to about $6 \times 10e10$. According to one embodiment, the initial dosing number of CFU is about $3 \times 10e10$. According to another embodiment, the dosing form may be a cultured beverage. Further, the dosing form may optionally be chosen from packets, capsules, tablets, or caplets.

DESCRIPTION

The present application relates to a unique strain of *Lactobacillus* bacteria deposited in the Agricultural Research Service Patent Culture Collection and given the NRRL Accession No. B-30892. In particular, the unique strain, discovered in the inventor's cultured beverage (or smoothie) cultures, has been identified as *Lactobacillus delbrueckii*, ssp. *bulgaricus*, and displays several unique characteristics when compared to other known species or strains of lactic acid producing bacteria.

I. Distinctive Characteristics of Novel Strain

Once identified as showing varying and beneficial characteristics to previous known strains of *Lactobacillus* bacteria, several tests were performed to (1) compare the acid producing characteristics of the new strain according to the present application, (2) compare the reproductive profile of the new strain according to the present application, and (3) identify the different colony, cell, and sensory morphology of the new strain according to the present application. Therefore, the following results were found.

A. Acid Production/Biological Activity

Figure 1:
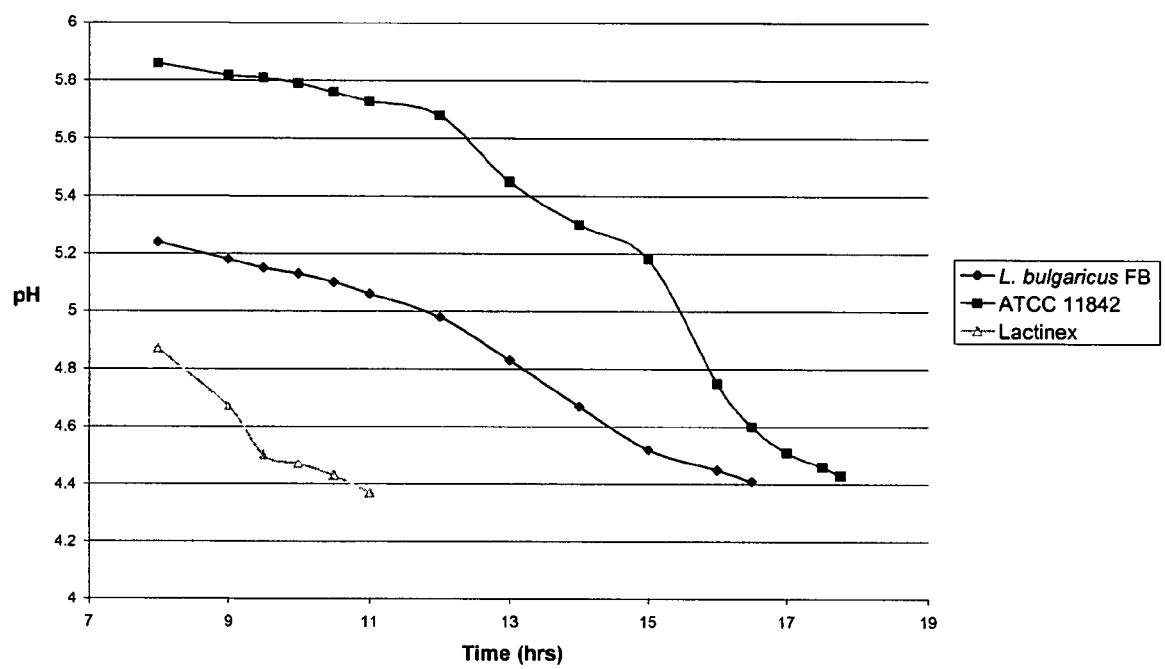
FIG. 1 is a line diagram showing the relative rates of lactic acid formation capability of three strains of *Lactobacillus delbrueckii*, ssp. *bulgaricus*, including the novel strain described herein.

Turning now to FIG. 1, a comparison graph showing the results of culturing three strains of *Lactobacillus bulgaricus* in bovine milk at a temperature of 40° Celsius, each of the three strains, designated as (1) "ATTC 11842" for a previously registered strain having the accession number ATTC 11842; (2) "Lactinex" for the commercially available strain that is readily available, and (3) "FB" for the strain according to the present application, having accession number NRRL B-30892. As borne out by the data embodied in FIG. 1 and Table 1 below, when 10% reconstituted non-fat bovine milk was inoculated with a 1% (by volume) inoculating culture from a seed vial that is not concentrated at 40° Celsius, each strain showed a substantial variation in the time required to meet the target pH of approximately 4.4. Since bacteria of the genus *Lactobacillus* are generally noted for their ability to convert the sugar lactose (present in most compositions referred to as milk) into lactic acid, the time it takes to reduce the pH of a lactose-containing culture from a consistent inoculation dose of the bacteria can be considered a defining characteristic or fingerprint of the biological activity of a particular strain. Further, a faster rate of fermentation (or lactic acid production) shown by a strain usually corresponds to a faster rate of reproduction of the number of colony forming units ("CFU's") of that strain, as shown in comparing FIG. 1 and FIG. 2.

As can be seen in Table 1, or the graphical comparison shown in FIG. 1, *L. bulgaricus* FB reached the targeted pH of 4.41 after 16.5 hours. It also yielded the second highest counts. Die off for FB occurred at pH of 4.45. *L. bulgaricus* ATTC 11842 reached the targeted pH last (after about 17.75 hrs) and yielded the lowest counts. It showed a die off after pH of 4.51. Lactinex reached the targeted pH the fastest after about 9.5 hours and yielded the highest counts. It also demonstrated a die off after pH of 4.50. Thus, as can be seen by the significant differences in time shown by each of the strains identified, the strain according to the current application is unique with regard to its biological activity rate.

TABLE 1 pH over time at 40° C. for the three strains of *L. bulgaricus* with a 1% transfer rate into milk

| | pH | | |
|---|---|---|---|
| Time (hrs) | *L. bulgaricus* FB | ATCC 11842 | Lactinex |
| 8 | 5.24 | 5.86 | 4.87 |
| 9 | 5.18 | 5.82 | 4.67 |
| 9.5 | 5.15 | 5.81 | 4.50 |
| 10 | 5.13 | 5.79 | 4.47 |
| 10.5 | 5.10 | 5.76 | 4.43 |
| 11 | 5.06 | 5.73 | 4.37 |
| 12 | 4.98 | 5.68 | |
| 13 | 4.83 | 5.45 | |
| 14 | 4.67 | 5.30 | |
| 15 | 4.52 | 5.18 | |
| 16 | 4.45 | 4.75 | |
| 16.5 | 4.41 | 4.60 | |
| 17 | | 4.51 | |
| 17.50 | | 4.46 | |
| 17.75 | | 4.43 | |

B. Colony Forming Unit Count Per Unit Time

Figure 2:
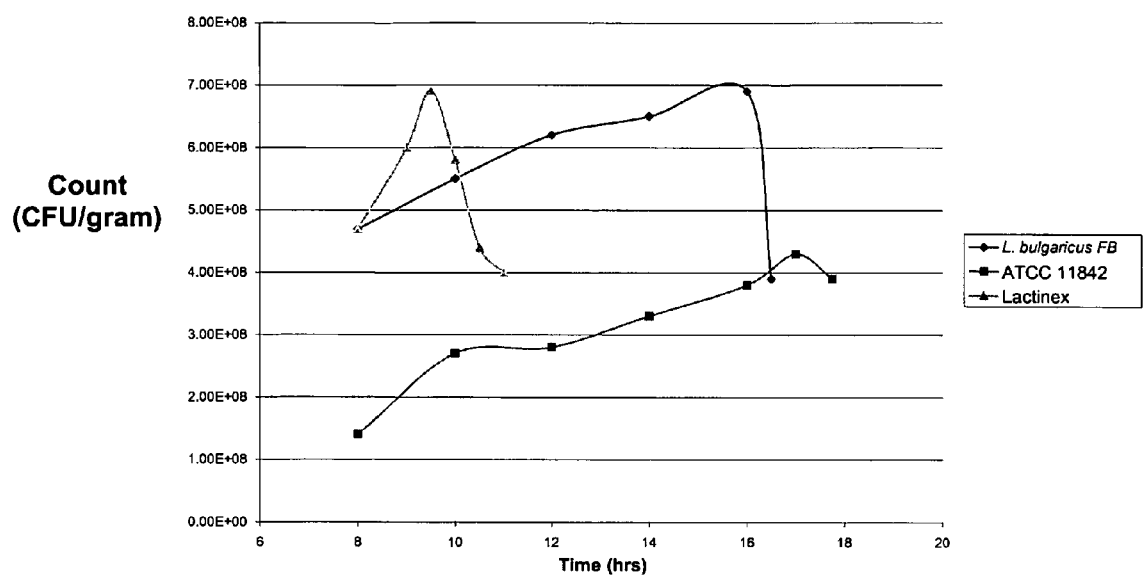
FIG. 2 is a line diagram showing the relative rates of colony increasing capability of three strains of *Lactobacillus delbrueckii*, ssp. *bulgaricus*, including the novel strain described herein.

Turning now to FIG. 2, a graphical comparison of the count versus time displayed by the three strains disclosed above, the three strains were cultured under conditions identical to those described above. Table 2 below shows the values plotted to obtain the graphical results in FIG. 2. As can be seen, each of the strains show significantly different rates of reproduction from one another, with a distinctly different time at which die-off occurs. Therefore, consistent with the results shown with regard to the pH profile of each strain, the number of colony forming units measured against time shows a distinct difference with regard to each strain.

TABLE 2

Count vs. Time for the Fermentation of Three Strains of *L. bulgaricus*

| | Count (cfu/gram) | | |
|---|---|---|---|
| Time (hrs) | *L. bulgaricus* FB | ATCC 11842 | Lactinex |
| 8 | 4.70E+08 | 1.4E+08 | 4.70E+08 |
| 9.0 | | | 6.00E+08 |
| 9.5 | | | 6.90E+08 |
| 10 | 5.50E+08 | 2.70E+08 | 5.80E+08 |
| 10.5 | | | 4.40E+08 |
| 11 | | | 4.00E+08 |
| 12 | 6.20E+08 | 2.80E+08 | |
| 14 | 6.50E+08 | 3.30E+08 | |
| 16 | 6.90E+08 | 3.80E+08 | |
| 16.5 | 3.9E+08 | | |
| 17 | | 4.30E+08 | |
| 17.75 | | 3.90E+08 | |

C. Cell Morphology, Colony Morphology, and Sensory Characteristics

Finally, turning to Table 3 below, the morphologies of the three strains were compared with regard to both colony formation and individual morphologies. As can be seen, while each of the strains exhibit the characteristic flavor associated with *Lactobacillus bulgaricus* fermentation the FB strain obtains a more tart flavor than the typical flavor shown by both Lactinex or ATCC when the optimal pH and CFU levels are reached. Additionally, both the cellular and colonial morphologies are very distinct from one another, further pointing to substantial differences in the FB strain over established strains.

TABLE 3

Morphological Comparison

| Bacterial Source | Colony Morphology | Cell Morphology | Sensory Characteristics |
|---|---|---|---|
| *L. bulgaricus* FB | Very small, round, beige, glossy colony | Long, curved, gram positive rods in singles | Typical *L. bulgaricus* acetaldehyde flavor; at desired CFU count, product has a lower pH and has a strong, tart flavor. |
| ATCC 11842 | Small, round, opaque colonies with rough edges | Medium gram positive, straight rods, in singles | Typical *L. bulgaricus* acetaldehyde flavor |

TABLE 3-continued

Morphological Comparison

| Bacterial Source | Colony Morphology | Cell Morphology | Sensory Characteristics |
|---|---|---|---|
| Lactinex | Medium to large, round, opaque colonies with rough edges | Medium to long gram positive, straight rods, in singles | Typical *L. bulgaricus* acetaldehyde flavor |

In addition to the above-noted characteristics of the novel FB strain according to the present application, it has been noted that the FB strain of *Lactobacillus bulgaricus* has shown biological activity within the digestive system of mammals in general, and humans in particular. Specifically, while the FB strain has shown itself to be a transitory inhabitant of the intestinal tract, it displays the ability to disrupt the bloom of pathogenic bacteria within the intestines of its host, decreases inflammatory response to irritants, may increase vitamin absorption, and shows general activity similar to those noted in the prior compositions discussed in U.S. Pat. No. 6,696,057, incorporated by reference herein.

II. Probiotic Compositions

Further in accordance with the present application, a probiotic composition operable to further the well-being of an individual ingesting the composition is presented. According to certain embodiments of the present application, the probiotic composition comprises a therapeutically effective number of colony forming units ("CFU's") of a *Lactobacillus* bacteria deposited in the Agricultural Research Service Patent Culture Collection and given the NRRL Accession No. B-30892 (also referred to herein as "*Lactobacillus delbrueckii*, ssp. *bulgaricus* 'FB'" or "*Lactobacillus bulgaricus* 'FB'")'. The probiotic composition optionally is a freeze-dried or frozen composition comprising the *Lactobacillus bulgaricus* 'FB' in a therapeutically effective amount.

According to certain aspects of the present application, a therapeutically effective amount of the *Lactobacillus bulgaricus* 'FB' comprises approximately $1 \times 10e6$ to about $2 \times 10e12$ CFU's of the bacteria. Further optionally, a therapeutically effective amount of the bacteria comprises about more than $1 \times 10e10$ CFU's, about more than $2 \times 10e10$ CFU's, about more than $3 \times 10e10$ CFU's, and/or about more than $4 \times 10e10$ CFU's of the bacteria. In one embodiment, a therapeutically effective amount may comprise $6 \times 10e10$ CFU's per day, and may be reached by dosing more than once per day. Further, a therapeutically effective amount may describe the concentration of the *Lactobacillus bulgaricus* 'FB' in a given media. For example, a therapeutically effective amount of *Lactobacillus bulgaricus* 'FB' may occur in a concentration about $1.3 \times 10e8$ CFU or more per gram of carbohydrate containing medium. According to other embodiments, a therapeutically effective concentration may be about $1.3 \times 10e8$ or less CFU per gram of carbohydrate-containing medium.

According to certain embodiments of the present application, the probiotic composition further comprises a carbohydrate-containing media whereby the *Lactobacillus bulgaricus* 'FB' strain is mixed into the carbohydrate-containing media. Optionally, a therapeutically effective amount of the bacteria is mixed with a given volume of the carbohydrate-containing media. Alternatively, an inoculating culture of the bacteria is added to the carbohydrate-containing media and conditions are provided so that the *Lactobacillus bulgaricus* 'FB' ferments the carbohydrate-containing media and increases the number of CFU's to at least a therapeutically effective amount of the bacteria. The carbohydrate-containing media may be milk or a milk product obtained from a lactating animal, a vegetable based milk or juice such as soy milk or carrot juice, may be a fruit juice or fruit drink, or any other carbohydrate-containing media.

While a therapeutically effective amount of bacteria may be embodied in a large volume of carbohydrate-containing media, according to one embodiment of the present application, the therapeutically effective number of bacteria is present in less than 24 fluid ounces of the carbohydrate-containing media. According to yet another embodiment, the therapeutically effective number of bacteria is present in less than 16 fluid ounces of the carbohydrate-containing media. Further according to yet another embodiment, the therapeutically effective number of bacteria is present in less than 12 fluid ounces of the carbohydrate-containing media. According to another embodiment, the therapeutically effective number of bacteria is present in less than 10 fluid ounces of the carbohydrate-containing media, or less than or equal to 8 fluid ounces of the carbohydrate-containing media. Finally, according to another embodiment, the therapeutically effective number of bacteria is present in less than 3.3 ounces of the carbohydrate-containing media.

It will be appreciated by those in the art that the *Lactobacillus bulgaricus* "FB" may be cultured by inoculating a large volume of the carbohydrate containing media under the proper conditions with less than 1% (by volume), less than or equal to 0.10% (by volume), or 0.05% (by volume) of concentrated *Lactobacillus bulgaricus* 'FB.' For example, Table 4 below shows the count versus time of CFU's formed at various inoculation rates, from frozen concentrated culture, in bovine milk at 40° Celsius. The composition is optionally fermented until the CFU's per target unit volume exceeds a therapeutically effective amount of the bacteria.

TABLE 4

Count vs. Time for the Fermentation *L. bulgaricus* FB at Varying Inoculation Rates

| | Count (CFU/gram) | | |
|---|---|---|---|
| Time (hrs) | 1.0% Inoculation Rate | 0.1% Inoculation Rate | 0.05% Inoculation Rate |
| 2 | 4.30E+08 | 1.70E+08 | 1.50E+07 |
| 4 | 9.60E+08 | 6.80E+08 | 4.80E+08 |
| 4.5 | 1.31E+09 | | |
| 5 | 1.00E+09 | | |
| 5.50 | 8.60E+08 | | |
| 6 | | 1.23E+09 | 1.03E+09 |
| 7.5 | | 1.04E+09 | |
| 8 | | 9.10E+08 | 1.22E+09 |
| 8.50 | | | 9.9E+08 |
| 9 | | | 9.50E+08 |

According to certain embodiments, the carbohydrate-containing medium comprises any such media common in the art.

For example only, the carbohydrate-containing medium is an animal or plant-based milk. For instance, reconstituted powdered bovine milk is used in one embodiment as the carbohydrate-containing media such that fermentation of the carbohydrate containing media results in a cultured beverage (or smoothie) with at least a therapeutically effective amount of the bacteria in a 10 ounce serving of the cultured beverage (or smoothie).

As will be appreciated in the art, in some cases it will be beneficial to provide more than a therapeutically effective amount of the bacteria per a target volume of the probiotic composition to ensure that the probiotic composition has a certain shelf life. As shown in Tables 5-7 below, the *Lactobacillus bulgaricus* 'FB' has been shown to have a shelf life approximately according to the values given in representative samples plated in MRS broth and in strawberry cultured beverage (or smoothie). Therefore, since the CFU numbers fall approximately according to the shelf rate schedule noted below, according to one embodiment, a probiotic composition is created with enough CFU's of the bacteria so that an therapeutically effective number of bacteria are available per target volume of the probiotic composition when it is administered to an individual.

Shelf Life Studies

*Lactobacillus bulgaricus* FB

TABLE 5

FB Sample Plated on MRS Broth

| Day | CFU/gram | CFU/10-ounces |
|---|---|---|
| 0 | 1.60E+09 | 4.8E+11 |
| 21 | 1.50E+09 | 4.5E+11 |
| 35 | 9.05E+08 | 2.72E+11 |
| 47 | 7.15E+08 | 2.15E+11 |
| 66 | 2.50E+08 | 7.5E+10 |

TABLE 6

FB Sample - Plated on MRS 5.4 Broth

| Day | CFU/gram | CFU/10-ounces |
|---|---|---|
| 0 | 1.85E+09 | 5.55E+11 |
| 21 | 7.50E+08 | 2.25E+11 |
| 35 | 3.05E+08 | 9.15E+10 |
| 47 | 1.60E+08 | 4.8E+10 |
| 66 | 8.50E+06 | 2.55E+09 |

TABLE 7

FB Sample - Cultured in Strawberry Fermented Beverage

| Day | CFU/gram | CFU/10-ounces |
|---|---|---|
| 0 | 1.70E+09 | 5.1E+11 |
| 14 | 1.36E+09 | 4.08E+11 |
| 20 | 8.95E+08 | 2.69E+11 |
| 30 | 6.75E+08 | 2.03E+11 |

The probiotic composition can take the final form of either liquid, solid, or semi-solid. For example, the probiotic composition may be a set or creamy cultured beverage (or smoothie). The probiotic composition may also be lyophilized and separated into specific dosing units. The dosing units may be packaged in one of several forms including but not limited to packets, capsules, tablets, or caplets. Any other packaging form as is common in the art may be utilized. Alternatively, the probiotic composition may be concentrated after fermentation is complete and then lyophilized prior to packaging. Prior to concentrating and lyophilizing the probiotic composition, the fermented end product can be packaged as a cultured beverage (or smoothie) as is typical in the art. After concentrating and lyophilizing, the probiotic composition can be packaged into desired dosing units. The packaged dosing units may be in any suitable form as is common in the art and can include, but not be limited to packets, capsules, caplets, or tablets.

III. Methods of Use of Novel Bacteria and/or Probiotic Composition

According to one embodiment of the present application the abovementioned *Lactobacillus delbrueckii*, ssp. *bulgaricus* bacterium given the NRRL Accession No. B-30892 and/or a probiotic composition according to one of the embodiments above is administered to an individual. According to one embodiment, the bacteria or probiotic is administered as part of a method for treating gastrointestinal disorders, hyperlipidemia, Irritable Bowel Syndrome, Inflammatory Bowel Disease, diarrhea; *C. difficile* associated disorders, antibiotic-associated diarrhea, Crohn's disease, ulcerative colitis, or an autoimmune disease. In addition, according to an embodiment of the present application, the bacteria or probiotic is administered as part of a method for boosting the immune system.

According to one embodiment, the method comprises the steps of providing a probiotic composition as disclosed above. The method further comprises administering the probiotic composition to an individual. Additionally, the method optionally comprises selecting a dosing form of the probiotic composition and determining an initial dosing strength and initial dosing frequency. For example, a therapeutically effective number of CFU's of the bacteria is selected for, as well as a target volume of a dosing media to determine dosing strength. For example, the dosing media may simply be freeze dried or frozen forms of the bacteria, and is optionally contained in a capsule or in a vial that allows consumption of the bacteria. According to another embodiment, the dosage strength of the composition is determined by the number of CFU's of the bacteria per unit volume of a carbohydrate-containing medium. For example, one initial dosing strength is more than 3×10e10 CFU's per 10 ounces of carbohydrate containing media. Another exemplary embodiment involves administering the aforementioned initial dosing strength at least twice per day, with the doses taken at least three hours between each administration.

According to another embodiment, yet an additional step in the method comprises determining the effectiveness of the probiotic composition in treating the patient. One optional step following this determination is to adjust both the dosing strength and the dosing frequency if positive results are not observed. Generally, determining the efficacy of the probiotic composition is determined by at least one option chosen from evaluating the improvement of the patient's clinical symptoms, or evaluating medically standard objective parameters as appropriate for a particular disorder. Such medically standard objective parameters include, but are not limited to, gastrointestinal imaging using, for example, endoscopy and barium x-ray studies, biopsy, histopathology, restoration of fluid and electrolyte balance, normalization of white blood count, serial stool analysis, and checking fasting plasma LDL, HDL and triglycerides.

Additionally, it will be appreciated by those skilled in the art that the probiotic composition or the bacteria is optionally administered when a patient shows no signs of disease or improper health. Such preventative administration is given in order to maintain or ensure proper health through maintaining a balance within the flora of the digestive system.

According to several clinical administrations of the bacteria and/or probiotic compositions disclosed herein, the following examples are given as situations in which the probiotic composition is effective or anticipated to be effective.

Example 1

A 40 year old female presented with a three-week history of watery diarrhea after being released from the hospital for a procedure to her skull. While the patient could not remember whether an antibiotic was administered to her during hospitalization, she had self-administered Imodium and *Lactobacillus acidophilus* without improvement of her symptoms. *Clostridium difficile* was confirmed in her system, indicating that the diarrhea was *C. difficile* associated disease (CDAD). A 10 day administration of metronidazole at 500 mg was administered three times per day with little positive effect. Thereafter, a probiotic composition according to the present application as described heretofore was administered for 10 days, twice daily with a CFU count of 5×10e10 per dose (or 5×10e9 CFU per gram). Upon completion of the probiotic regimen, a complete resolution of the symptoms was observed in the patient, with no relapses in over one year.

Example 2

A 64 year old female presented with a 10 day history of watery diarrhea, cramping, and flatus, which was confirmed to be caused by CDAD by way of a *C. difficile* toxin assay. Consistent with Example 1, metronidazole was prescribed for 10 days, with no improvements. Further similarly to Example 1, a probiotic composition according to the present application as described heretofore was administered for 10 days, twice daily with a CFU count of 5×10e10 per dose (or 5×10e9 CFU per gram). The patient improved initially, but had recurrence of diarrhea after having levaquin administered for a urinary tract infection. Continued dosing with the probiotic composition partially alleviated the diarrhea suspected as a result of recurrent CDAD. Additional medication with Fibercon and levsinex finally alleviated the remaining diarrhea symptoms, suspected to be associated with a flare up of irritable bowel syndrome.

Example 3

A 76 year old female presented with a four week history of loose stools and hematochelzia. The patient had a history of bleeding hemorrhoids and was currently using Plavix® as treatment for transient ischemic attacks. The patient tested positive for CDAD, and was given the standard 10 day cycle of metronidazole with only slight improvement, with diarrhea persisting even after an additional 7 day cycle of metronidazole. Similarly to Example 1, a probiotic composition according to the present application as described heretofore was administered for 10 days, twice daily with a CFU count of 5×10e10 per dose (or 5×10e9 CFU per gram). Upon completion of the probiotic regimen, a complete resolution of the symptoms was observed in the patient, with no relapses in over one year.

Example 4

An 84 year old male presented with bloody diarrhea. A colonoscopy showed extensive diverticular disease and a single tubular adenoma. The patient was released from hospitalization when bleeding ceased, but returned when the diarrhea persisted. The patient tested positive for CDAD, and was administered a probiotic composition according to the present application as described heretofore for 10 days, twice daily with a CFU count of 5×10e10 per dose (or 5×10e9 CFU per gram). The patient had complete resolution of diarrhea and has not relapsed in over one year.

Example 5

A 36 year old female with a four week history of diarrhea presented. The symptoms presented after administration of Floxin® for a urinary tract infection and Cleocin® vaginal cream for bacterial vaginosis. The patient was administered metronidazole for 10 days, and was then given vancomycin at 125 mg for 14 days, with no success. The patient was administered a probiotic composition according to the present application as described heretofore for 10 days, twice daily with a CFU count of 5×10e10 per dose (or 5×10e9 CFU per gram). The patient had complete resolution of diarrhea and has not relapsed in over fifteen months.

Example 6

Female patient in her 40's presented with ulcerative colitis. Patient was thereafter administered a probiotic composition according to the present application as described heretofore twice daily with a CFU count of 5×10e10 per dose (or 5×10e9 CFU per gram) with improvement noted by the patient. Shortly after improvement, patient withdrew from the study.

Example 7

A 52 year old male presented with severe pancolitis for ten years on conventional therapies. Patient was thereafter administered a probiotic composition according to the present application as described heretofore, twice daily with a CFU count of 5×10e10 per dose (or 5×10e9 CFU per gram) with improvement noted by the patient. Patient experienced dramatic improvement in symptoms, and after nine months of treatment was able to taper off the corticosteroids and 5-ASA agents, and was able to be maintained on Imuran® alone.

Example 8

A 40 year old male patient with active distal ulcerative colitis presented. While initial improvement on traditional corticosteroid treatment was seen, relapses occurred. Patient was thereafter administered a probiotic composition according to the present application, achieving remission for 13 months. Patient thereafter switched to a freeze-dried composition according to the present application, remaining in remission. Currently, the patient remains symptom free, and has switched to a liquid probiotic composition according to the present application.

Example 9

A 40+ year old female with active Crohn's disease presented, despite currently being administered Asacol®. Patient was thereafter administered a probiotic composition according to the present application as described heretofore, twice daily with a CFU count of 5×10e10 per dose (or 5×10e9 CFU per gram) with improvement noted by the patient. The patient experienced significant relief from her symptoms, with no progression of the disease noted. Currently, the disease activity is mild and stable. Since 2004, the patient has continued using the probiotic, and continues to experience relief from the disease.

Example 10

A 40+ year old male with active case of Ulcerative Colitis was being treated with Cortenema®. Thereafter, he was given a probiotic composition according to the present application as described heretofore, twice daily with a CFU count of 5×10e10 per dose (or 5×10e9 CFU per gram). After one year on the probiotic composition, complete remission was achieved, and all medications were stopped. Remission remained for over one year, with a flare up of the condition occurring thereafter. The patient was treated initially with Prednisone and a 5-ASA agent but did not have success. The patient was restarted on the probiotic composition and Cortenema® and tapered off both prednisone and the 5-ASA agent. The patient is currently taking only the probiotic composition and still remains in remission.

Example 11

In addition to the above, multiple patients have been administered one or more probiotic composition according to the present invention, with each patient noting significant boost to their immune systems, including relief from sinus infections, fewer incidences or shorter durations of influenza, gastroenteritis, and other respiratory infections.

Although the present application has been described in considerable detail with reference to certain preferred versions thereof. Therefore, the spirit and scope of the appended claims should not be limited to the description of the preferred versions contained herein.

What is claimed is:

1. An isolated culture of the bacterial strain *Lactobacillus delbrueckii*, ssp. *bulgaricus* having accession number NRRL B-30892.

2. An isolated culture of a bacterial strain of the genus *Lactobacillus*, having all of the identifying characteristics of the *Lactobacillus* bacteria deposited in the Agricultural Research Service Patent Culture Collection and given the NRRL Accession No. B-30892.

3. A probiotic composition comprising *Lactobacillus delbrueckii*, ssp. *bulgaricus* in a carbohydrate-containing medium, the *Lactobacillus delbrueckii*, ssp. *bulgaricus* having accession number NRRL B-30892, whereby the probiotic composition contains a therapeutically effective dose of *Lactobacillus delbrueckii*, ssp. *bulgaricus* having accession number NRRL B-30892 to eliminate alleviate the symptoms of *Clostridium difficile* associated disease.

4. The probiotic composition of claim 3, wherein the therapeutically effective dose is at least about 1.3×10e10 colony forming units in 24 ounces or less of the carbohydrate-containing medium.

5. The probiotic composition of claim 4, wherein the carbohydrate-containing medium is a milk-based product.

6. The probiotic composition of claim 5, wherein the milk-based product is a vegetable milk or milk derived from an animal.

7. The probiotic composition of claim 4 wherein the therapeutically effective dose of *Lactobacillus delbrueckii*, ssp. *bulgaricus* is at least about 1.4×10e10 colony forming units.

8. The probiotic composition of claim 7, wherein the therapeutic dose of *Lactobacillus delbrueckii*, ssp. *bulgaricus* is at least about 3×10e10 colony forming units.

9. The probiotic composition of claim 7, wherein the therapeutic dose of *Lactobacillus delbrueckii*, ssp. *bulgaricus* is in about 10 ounces or less of the composition.

10. The probiotic composition of claim 7, wherein the therapeutically effective dose effectively alleviates the symptoms of a diseased state selected from the group consisting of Crohn's disease, ulcerative colitis, irritable bowel syndrome, inflammatory bowel disease, diarrhea, hyperlipidemia, hypovitaminosis, antibiotic-associated diarrhea, and *Clostridium difficile* associated disease.

* * * * *